United States Patent [19]

Wysocki

[11] 4,269,666

[45] May 26, 1981

[54] RECOVERY OF ACRYLIC ACID BY REVERSAL OF ACRYLIC ACID/WATER RELATIVE VOLATILITY

[75] Inventor: Carl G. Wysocki, North Royalton, Ohio

[73] Assignee: Standard Oil Company, Cleveland, Ohio

[21] Appl. No.: 6,056

[22] Filed: Jan. 24, 1979

[51] Int. Cl.³ .......................................... C07C 51/44
[52] U.S. Cl. ...................................... 203/15; 203/50; 562/600
[58] Field of Search .................. 203/15, 50; 562/600

[56] References Cited

U.S. PATENT DOCUMENTS

| 2,922,815 | 1/1960 | Faerber et al. | 203/62 |
| 3,846,488 | 11/1974 | Otsuki et al. | 203/15 |

Primary Examiner—Frank Sever
Attorney, Agent, or Firm—Herbert D. Knudsen; David J. Untener; Larry W. Evans

[57] ABSTRACT

An aqueous solution of acrylic acid and water containing 30 wt. % or less acrylic acid, can be concentrated to 40–60 wt. % acrylic acid in the overhead of a distillation column through the addition of certain salts that reverse the relative volatility between acrylic acid and water. Suitable salts can be ferrous, lithium and calcium chlorides.

9 Claims, 3 Drawing Figures

RECOVERY OF ACRYLIC ACID BY REVERSAL OF ACRYLIC ACID/WATER RELATIVE VOLATILITY

BACKGROUND OF THE INVENTION

Salts have been used for a variety of reasons to aid in the separation of acrylic acid and water.

The predominate use of salts has been to allow simple phase separation that results in a first phase containing 80 wt.% or more acrylic acid with water, and a second phase containing approximately 10 wt.% acrylic acid, water and the salt. U.S. Pat. No. 2,922,815 discloses that in the prior art, such drying agents as calcium chloride and sodium sulfate have been used to increase the concentration of acrylic acid-water systems from 35–40 wt.% acrylic acid to 50–60 wt.% acrylic acid. Further, nickel chloride or nickel bromide can be used to achieve concentrations of up to 80%.

U.S. Pat. No. 3,663,375, although directed to the separation of methacrylic acid from water, discloses a process suitable for the separation of acrylic acid wherein sodium sulfate is first mixed with the acid, followed by a two-phase separation. Both phases are then passed to separate distillation columns wherein the acid is removed from the rich phase, and a stream of water, salt and some acid removed from the dilute phase. However, use of sodium sulfate or sulfuric acid with acrylic acid has shown little or no phase separation. Thus, while the processing steps may be similar, different acids would have to be utilized.

U.S. application Ser. No. 860,516 discloses the use of aluminum chloride to achieve a 95 wt.% concentration of acrylic acid in the rich phase from an aqueous solution containing 50 wt.% acrylic acid.

Salts have also been shown to have other effects on acrylic acid-water solutions. U.S. Pat. No. 3,846,488 discloses that certain salts at low concentrations reduce the amount of time necessary for the separation of the phases to occur. U.S. application Ser. No. 860,937 discloses certain salts that eliminate the eutectic point of an aqueous acrylic acid solution, thereby allowing fractional crystallization.

It is also known that certain solvents, such as ethyl acetate, can extract acrylic acid from the aqueous solution using liquid-liquid separation (see U.S. Pat. No. 3,344,178). U.S. Pat. No. 3,846,488 notes that this liquid extraction efficiency can be increased by the addition of salts that affect the liquid-liquid equilibrium.

While the above salts have been effective in concentrating acrylic acid in the rich phase, there still remains a dilute acrylic acid phase, usually containing 20 wt.% or less acrylic acid, saturated with salt. Because of the relative volatilities between acrylic acid and water, fractional distillation of this stream is difficult and substantial losses of acrylic acid are realized in the separation. This is because acrylic acid is always more concentrated in the liquid than in the vapor in equilibrium with it.

It has been discovered that certain salts, independent of any solvents, can substantially reverse the relative volatility of acrylic acid and water, thus allowing a simple method of concentrating dilute acrylic acid solutions.

SUMMARY OF THE INVENTION

The invention may be stated as being a method for increasing the concentration of an aqueous acrylic acid solution containing 30 wt.% or less acrylic acid, comprising the steps of:

(a) dissolving in said aqueous acrylic acid solution a salt, said salt characterized in that upon boiling a salt saturated 10 wt.% acrylic acid aqueous solution to obtain a vapor and a liquid component at equilibrium, the wt.% acrylic acid in the vapor is greater than the wt.% acrylic acid in the liquid;

(b) distilling said salt containing acrylic acid solution to obtain a vapor stream containing acrylic acid and a liquid stream free of acrylic acid.

The invention may also be stated as a method for separating acrylic acid from a mixture of acrylic acid and water comprising the steps of:

(a) dissolving in said mixture a salt in an amount sufficient to salt out the mixture to form a concentrated acrylic acid phase, and a dilute acrylic acid phase containing 20 wt.% or less acrylic acid, said salt characterized in that upon boiling a salt saturated 10 wt.% acrylic acid aqueous solution to obtain a vapor and a liquid component at equilibrium, the wt.% acrylic acid in the vapor is greater than the wt.% acrylic acid in the liquid;

(b) separating the concentrated phase from the dilute phase; and (c) distilling said dilute phase to obtain a vapor stream containing acrylic acid in a liquid stream free from acrylic acid.

As noted above, a relatively easy test can be utilized to determine if a salt has the ability to reverse the relative volatility of acrylic acid and water. A 10 wt.% solution of acrylic acid and water, when boiled to obtain a vapor and a liquid component at equilibrium, will have a higher wt.% acrylic acid in the liquid than in the vapor. By saturating the 10 wt.% solution with salt, and boiling to obtain the vapor and liquid components, a measurement of the relative wt.% of acrylic acid in the vapor and the liquid will determine if a salt reverses the relative volatility.

Figure 1:
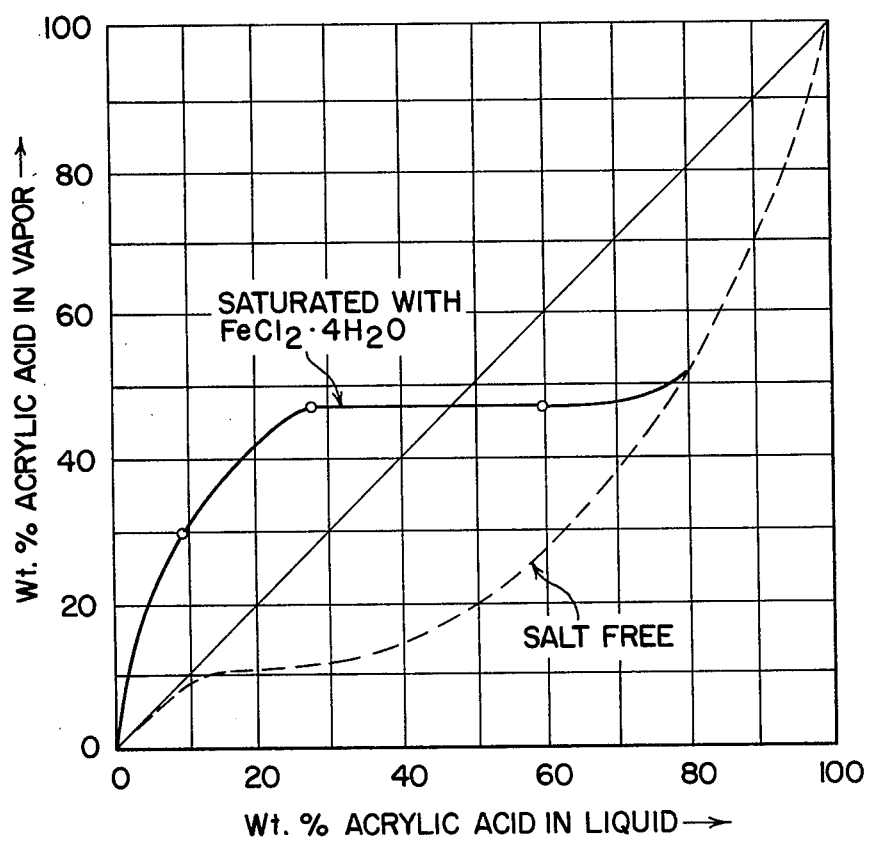
FIG. 1 and FIG. 2 are graphs showing the vapor liquid equilibrium of a salt-free acrylic acid/water system as compared to such systems saturated with iron chloride and lithium chloride, respectively.

As can be seen in FIG. 1, a salt-free acrylic acid in water solution is always to the right of the diagonal line. This curve indicates that acid is always more concentrated in the liquid than in the vapor in equilibrium with it. Whenever the curve of the solution crosses or touches the diagonal line, an azeotrope exists. It is not possible to fractionally distill two components through an azeotrope. Thus, while it may be possible to achieve a purity of 90% or greater acrylic acid in the bottom product of a distillation column, the loss of acrylic acid to the overhead is fairly high.

Figure 2:
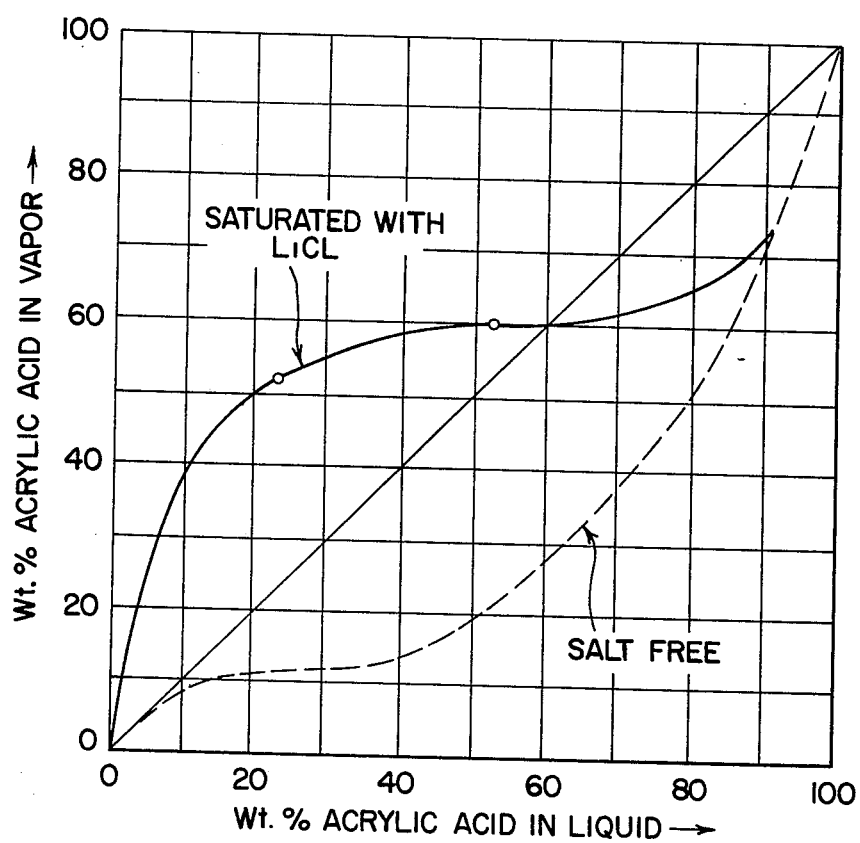

As can be seen in FIGS. 1 and 2, when the acrylic acid aqueous solution is saturated with $FeCl_2 \cdot 4H_2O$ or LiCl, the curve denoting volatility is dramatically shifted to the left of the diagonal. This allows dilute aqueous acrylic acid solutions to be increased in concentration up to 40–60% before reaching the azeotrope. Because of the relocation of the azeotrope, the bottoms of the distillation column can now be free of acrylic acid, thus reducing losses to the system.

Figure 3:
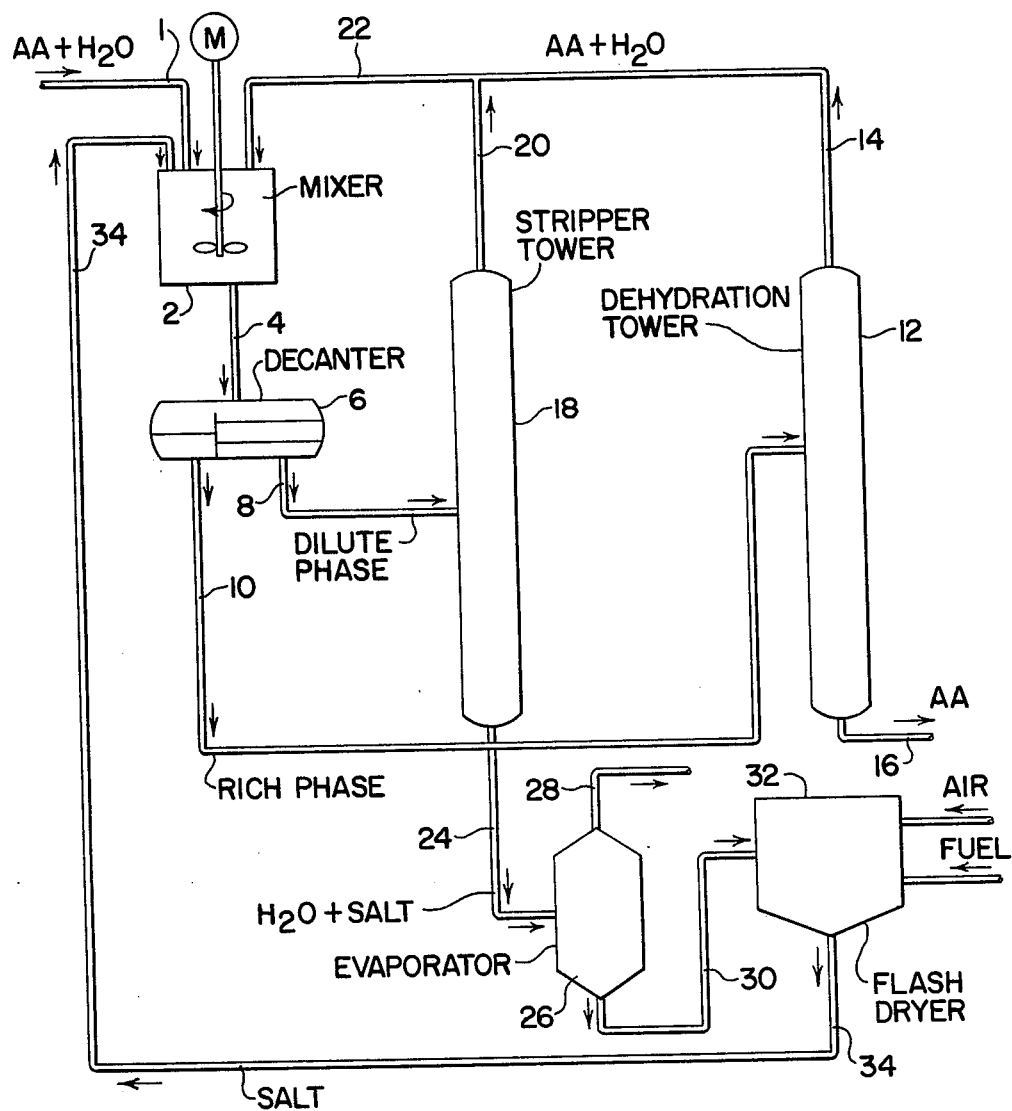
FIG. 3 is a process flow diagram disclosing a method for purifying acrylic acid utilizing the present invention.

FIG. 3 discloses a process for purifying acrylic acid utilizing the present invention. A 30-60 wt.% acrylic acid aqueous solution is passed through line 1 to mixer 2. Also entering mixer 2, is recycled salt through line 34 and the recycled dilute acrylic acid streams, later to be identified.

After the salt has been dissolved in the solution, it is then passed through line 4 to decanter 6. In the decanter, a phase separation occurs wherein a rich phase containing 80 wt.% or more acrylic acid with water, and a dilute phase containing 10-15 wt.% acrylic acid, water and salt are formed.

The rich phase is removed from the decanter through line 10 and passes to the dehydration tower 12. Water-free acrylic acid is removed from the bottom of the tower through line 16, and an overhead stream containing approximately 15% acrylic acid with water is removed through line 14 and recycled back to the mixer.

The dilute phase in the decanter is removed through line 8 and passed to stripper 18. Because the salt has reversed the relative volatility of the solution, a stream containing 40 wt.% or more acrylic acid with water can be removed overhead through line 20 and recycled back to the mixer through line 22. The bottoms of the stripper tower, being water, salt and almost completely acid free, is passed through line 24 to evaporator 26. Water is removed as a vapor through line 28 from the evaporator, and the salt then passes through line 30 to flash dryer 32 for final water removal. The salt is then recycled through line 34 back to the mixer for reuse.

Salts that have shown to be effective in reversing volatility of the solutions are LiCl, NaCl, $CaCl_2$, $FeCl_2$, $CoCl_2$, $NiCl_2$, KCl, KI, KBr and $(NH_4)_2SO_4$. However, salts such as KF and $NH_4HSO_4$ do not have this desired quality.

While it is preferred that the salt also have the ability to perform a phase separation of the more concentrated acrylic acid solution, this quality is not necessary. Salts such as NaCl, KCl, KF and KBr, do not bring about such phase separation. Thus the present invention is applicable to many known processes for the recovery of acrylic acid from dilute streams even if phase separation is not used.

Preferred salts useful in the invention are calcium chloride, lithium chloride and ferrous chloride, most preferred being ferrous chloride. While the calcium and lithium salts, specifically lithium, allows a reversal up to approximately 60 wt.% equilibrium, these salts have shown some polymer formation problems.

As noted above, the present invention can be utilized by simply dissolving the salt in a dilute aqueous acrylic acid solution containing 30 wt.% or less acrylic acid. It is preferred, however, to use a salt that both reverses the relative volatility and performs a phase separation of acrylic acid and water. This process is depicted in FIG. 3 and is somewhat similar to U.S. Pat. No. 3,663,375. In either method, however, the amount of salt contained in the acrylic acid aqueous solution to be distilled is in the range of 5-35 wt.%.

By utilizing the salts of the present invention, the acrylic acid contained in the dilute phase can be completely recovered and recycled back to the phase separation step. Since less water is recycled, this serves not to dilute the original solution to the extent found in the prior art. Further, because of the dramatic reversal as shown with such salts as ferrous or lithium chloride, the distillation column necessary for this separation requires far less trays than has been known in the art.

EXAMPLE 1

Effect of Salts on Distillation of Dilute Phase 30 wt.% solutions of acrylic acid and water were saturated with $LiCl_2$, $FeCl_2$ and $CaCl_2$, respectively. For example, 63 grams of $FeCl_2.4H_2O$ was added to 215.5 grams of the 30 wt.% solution to obtain saturation.

To show the effects of a single phase distillation, the acid-salt solution was heated in an Othmer still at a pressure of 2.51 psia. Equilibrium was reached when the temperature of the liquid and the vapor was constant for approximately an hour, depending upon the boiling rate. The heat source and the vacuum was then turned off, and a condensed vapor sample was immediately taken. A liquid sample was similarly taken and cooled in a cooled water bath. The wt.% acid was determined by titration with sodium hydroxide. This wt.% includes the salt in the total solution. The results of these experiments are shown in Table I.

TABLE I

One-Stage Distillation of Acid-Salt Solutions

| Salt | Acrylic Acid Wt. % in Overhead |
|---|---|
| $LiCl_2$ | 54 |
| $FeCl_2$ | 47 |
| $CaCl_2$ | 43 |

As can be seen above, the overhead product can be concentrated from 30% to 54% acrylic acid in a single stage. When using lithium chloride, 60 wt.% acrylic acid in the overhead can be achieved with multiple stages. Further concentrations of the acrylic acid by distillation is, however, limited by an azeotrope.

EXAMPLE 2

Summary of Various Salts

In the same manner as Example 1, a 30% aqueous acrylic acid solution saturated with the respective salt was prepared. Vapor-liquid equilibrium experiments were then carried out in the Othmer still as detailed in Example 1. A 30 wt.% aqueous acrylic acid solution was then prepared and again saturated with the corresponding salt to determine the salt's capability for phase separation. The results of this experiment are shown in Table II. The wt.% acrylic acid in the liquid includes the salt. The phase separation was carried out at 25° C.

TABLE II

SUMMARY OF SALTS IN 30% AQUEOUS ACRYLIC ACID SOLUTION SATURATED WITH SALT

| Salt | Wt. % Salt | Wt. % AA In Liq. | Wt. % AA In Vap. | Boiling Temp. | Phase Sep |
|---|---|---|---|---|---|
| — | — | 38.3 | 15.6 | 58.5 | |
| LiCl | 15.3 | 22.8 | 52.1 | 65 | Yes |
| NaCl | 16.6 | 23.8 | 37.8 | 61 | No |
| KCl | 15.4 | 24.9 | 29.3 | 61 | No |
| $CaCl_2$ | 16.1 | 31.9 | 43.6 | 61.5 | Yes |
| $FeCl_2.4H_2O$ | 22.6 | 27.4 | 46.9 | 60 | Yes |
| $CoCl_2.6H_2O$ | 21.1 | 23.9 | 30.1 | 60 | Yes |
| $NiCl_2.6H_2O$ | 24.0 | 25.7 | 34.7 | 59.5 | |
| KF | 20.9 | 24.0 | 9.4 | 63.5 | No |
| KCl | 15.4 | 24.9 | 29.3 | 61 | No |
| KBr | 27.4 | 20.8 | 30.4 | 61 | No |
| KI | 45.2 | 16.5 | 31.3 | 63 | No |
| $(NH_4)_2SO_4$ | 29.5 | 21.3 | 37.4 | 60.5 | |
| $NH_4HSO_4$ | 14.2 | 31.0 | 28.1 | 59.5 | |

As can be seen in the above Table, a 30% aqueous acrylic acid solution without salt addition contains more acrylic acid in the liquid phase than in the corresponding vapor phase. Certain salts such as lithium chloride dramatically reverse this concentration, whereas salts like KF do not. Further, the Table shows that salts that do reverse the concentrations do not necessarily achieve phase separations. Sodium chloride, while reversing the relative volatility, did not result in the separation of phases.

It is not necessary to saturate the acrylic acid solution to achieve this reversal effect. When the amount of salt added is below the saturation level, the azeotrope is not as high as when the solution is saturated. This results in a reduction of the maximum wt.% acrylic acid that can be achieved in the overhead vapor. For example, when an acrylic acid solution is saturated with calcium chloride, the azeotrope exists at approximately 43 wt.% acrylic acid in both the liquid and the vapor. When 75% of the amount of calcium chloride needed to saturate the solution is added, the azeotrope drops to approximately 36%. Finally, when one-half of the amount of salt necessary for saturation is added, the azeotrope is lowered to approximately 30%.

We claim:

1. A method for increasing the concentration of an organic solvent free aqueous acrylic acid solution having 30 wt.% or less acrylic acid, comprising
   (a) performing a first step consisting of dissolving in said aqueous acrylic acid solution a salt, said salt characterized in that upon boiling a salt saturated 10 wt.% acrylic acid aqueous solution to obtain a vapor and a liquid component at equilibrium, the wt.% acrylic acid in the vapor is greater than the wt.% acrylic acid in the liquid; and
   (b) distilling said salt containing acrylic acid solution to obtain a vapor stream containing acrylic acid and a liquid stream free of acrylic acid.

2. The method of claim 1 wherein the salt is selected from the group consisting of lithium chloride, calcium chloride, iron chloride, sodium chloride, potassium chloride, cobalt chloride, nickel chloride, KI and $(NH_4)_2 SO_4$.

3. The method of claim 2 wherein the salt is iron chloride.

4. The method of claim 1 wherein the acrylic acid solution contains 15 wt.% or less acrylic acid.

5. The method of claim 1 wherein distilling of the salt containing acrylic acid solution occurs in a distillation column having fewer than ten trays.

6. A method for separating acrylic acid from an organic solvent free mixture of acrylic acid and water comprising the steps of:
   (a) performing a first step consisting of dissolving in said mixture a salt in an amount sufficient to salt out the mixture to form a concentrated acrylic acid phase, and a dilute acrylic acid phase containing 20 wt.% or less acrylic acid, said salt characterized in that upon boiling a salt saturated 10 wt.% acrylic acid aqueous solution to obtain a vapor and a liquid component at equilibrium, the wt.% acrylic acid in the vapor is greater than the wt.% acrylic acid in the liquid;
   (b) separating the concentrated phase from the dilute phase; and
   (c) distilling said dilute phase to obtain a vapor stream containing acrylic acid and a liquid stream free from acrylic acid.

7. The method of claim 6 wherein the salt is selected from the group consisting of lithium chloride, calcium chloride, iron chloride, sodium chloride, potassium chloride, cobalt chloride, nickel chloride, KI and $(NH_4)_2 SO_4$.

8. The method of claim 7 wherein the acrylic acid solution contains 15 wt.% or less acrylic acid.

9. The method of claim 6 wherein distilling of the salt containing acrylic acid solution occurs in a distillation column having fewer than ten trays.

* * * * *